United States Patent [19]

Marko et al.

[11] Patent Number: 4,965,364

[45] Date of Patent: Oct. 23, 1990

[54] LIGAND-ACCELERATED CATALYTIC ASYMMETRIC DIHYDROXYLATION

[75] Inventors: Istvan E. Marko, Sheffield, England; K. Barry Sharpless, Brookline, Mass.

[73] Assignee: Massachusetts Institute of Technology, Cambridge, Mass.

[21] Appl. No.: 250,378

[22] Filed: Sep. 28, 1988

Related U.S. Application Data

[63] Continuation-in-part of Ser. No. 159,068, Feb. 23, 1988, which is a continuation-in-part of Ser. No. 142,692, Jan. 11, 1988, abandoned.

[51] Int. Cl.$^5$ .................. C07D 453/02; C07D 453/04; C07C 215/34; C07C 33/26
[52] U.S. Cl. ..................................... 546/134; 560/38; 564/355; 564/373; 568/811; 568/822
[58] Field of Search .................. 560/38; 568/811, 822; 564/355, 373; 546/134

[56] References Cited

U.S. PATENT DOCUMENTS

| | | | |
|---|---|---|---|
| 4,482,763 | 11/1984 | Austin et al. | 568/811 |
| 4,486,613 | 12/1984 | Michaelson et al. | 568/811 |
| 4,496,778 | 1/1985 | Myers et al. | 568/860 |
| 4,496,779 | 1/1985 | Myers et al. | 568/860 |

FOREIGN PATENT DOCUMENTS

WO89/02428  6/1988  PCT Int'l Appl. .................. 546/134

OTHER PUBLICATIONS

E. N. Jacobsen et al., *J. American Chemical Society*, 110: 1968–1970 (1988).
K. B. Sharpless and K. Akashi, *J. American Chemical Society*, 98(7):1986–1987 (1976).
K. Akashi et al., *J. Organic Chemistry*, 43(10):2063–2066 (1978).
E. Herranz and K. B. Sharpless, *J. Organic Chemistry*, 43(12):2544–2548 (1978).
B. A. Cartwright et al., *J.C.S. Chem. Comm.*, pp. 853–854 (1978).
R. Collin et al., *Biochimica et Biophysica Acta*, 354:152–154 (1974).

V. Van Rheenen et al., *Tetrahedron Letters*, 23:1973–1976 (1976).
R. Ray and D. S. Matteson, *Tetrahedron Letters*, 21:449–450 (1980).
S. G. Hentges and K. B. Sharpless, *J. American Chemical Society*, 102(12):4263–4265 (1980).
H. S. Mosher and J. D. Morrison, *Science*, 221:1013–1019 (1983).
T. H. Maugh, *Science*, 221:351–354 (1983).
R. Criegee, *J. Liebigs. Ann. Chem.*, 522:75–96 (1936).
N. Iwasawa et al., *Chemistry Letters*, pp. 1721–1724 (1988).

(List continued on next page.)

*Primary Examiner*—Alan L. Rotman
*Assistant Examiner*—Joseph K. McKane
*Attorney, Agent, or Firm*—Hamilton, Brook, Smith & Reynolds

[57] ABSTRACT

An osmium-catalyzed method of addition to an olefin. In the method of asymmetric dihydroxylation of the present invention, an olefin, a chiral ligand, an organic solvent, water, an amine oxide an osmium-containing compound and, optionally a tetraalkyl ammonium compound are combined. In the method of asymmetric oxyamination of the present invention, an olefin, a chiral ligand, an organic solvent, water, an amine derivative, an osmium-containing compound and, optionally, a tetraalkyl ammonium compound are combined. In the method of asymmetric diamination of the present invention, an olefin, a chiral ligand, an organic solvent, a metallo-chloramine derivative or an amine derivative and an osmium-containing compound are combined. In one embodiment, an olefin, a chiral ligand which is a dihydroquinidine derivative or a dihydroquinine derivative, acetone, water, N-methyl morpholine N-oxide and osmium tetroxide are combined to effect asymmetric dihydroxylation of the olefin.

11 Claims, 4 Drawing Sheets

OTHER PUBLICATIONS

K. B. Sharpless et al., *J. American Chemical Soc.*, 97:2305–2307 (1975).

K. B. Sharpless et al., *J. Organic Chemistry*, 41:177–179 (1975).

A. O. Chong et al., *J. Am. Chem. Soc.*, 99:3420–3426 (1977).

E. Herranz et al., *J. Am. Chem. Soc.*, 100:3596–3598 (1978).

M. Schroder, *Chem. Rev.*, 80:187–213 (1980).

T. Yamada and K. Narasaka, *Chem. Letters*, 131–134 (1986).

K. B. Sharpless, *Chemistry in Britain* (Jan. 1986).

M. Tokles and J. K. Snyder, Tetrahedron Letters, 27:3951–3954 (1986).

Y. Gao, et al., *J. Am. Chem. Soc.*, 109:5765–5779 (1987).

Ab. A. Smaardijk and H. Wynberg, *J. Org. Chem.*, 52:135–137 (1987).

K. Tomioka et al., *j. Am. Chem. Soc.*, 109:6213–6215 (1987).

LIGAND-ACCELERATED CATALYTIC ASYMMETRIC DIHYDROXYLATION

RELATED APPLICATIONS

This is a continuation-in-part of application U.S. Ser. No. 159,068, filed Feb. 23, 1988, which is a continuation-in-part of application U.S. Ser. No. 142,692, filed Jan. 11, 1988, now abandoned.

FUNDING

Work described herein was supported by a grant from the National Institutes of Health.

BACKGROUND

In nature, the organic constituents of animals, microorganisms and plants are made up of chiral molecules, or molecules which exhibit handedness. Enantiomers are stereoisomers or chiral molecules whose configurations (arrangements of constituent atoms) are mirror images of each other; absolute configurations at chiral centers are determined by a set of rules by which a priority is assigned to each substituent and are designated R and S. The physical properties of enantiomers are identical, except for the direction in which they rotate the plane of polarized light: one enantiomer rotates plane-polarized light to the right and the other enantiomer rotates it to the left. However, the magnitude of the rotation caused by each is the same.

The chemical properties of enantiomers are also identical, with the exception of their interactions with optically active reagents. Optically active reagents interact with enantiomers at different rates, resulting in reaction rates which may vary greatly and, in some cases, at such different rates that reaction with one enantiomer or isomer does not occur. This is particularly evident in biological systems, in which stereochemical specificity is the rule because enzymes (biological catalysts) and most of the substrates on which they act are optically active.

A mixture which includes equal quantities of both enantiomers is a racemate (or racemic modification). A racemate is optically inactive, as a result of the fact that the rotation of polarized light caused by a molecule of one isomer is equal to and in the opposite direction from the rotation caused by a molecule of its enantiomer. Racemates, not optically active compounds, are the products of most synthetic procedures. Because of the identity of most physical characteristics of enantiomers, they cannot be separated by such commonly used methods as fractional distillation (because they have identical boiling points), fractional crystallization (because they are equally soluble in a solvent, unless it is optically active) and chromatography (because they are held equally tightly on a given adsorbent, unless it is optically active). As a result, resolution of a racemic mixture into enantiomers is not easily accomplished and can be costly and time consuming.

Recently, there has been growing interest in the synthesis of chiral compounds because of the growing demand for complex organic molecules of high optical purity, such as insect hormones and pheromones, prostaglandins, antitumor compounds, and other drugs. This is a particularly critical consideration, for example, for drugs, because in living systems, one enantiomer functions effectively and the other enantiomer has no biological activity and/or interferes with the biological function of the first enantiomer.

In nature, the enzyme catalyst involved in a given chemical reaction ensures that the reaction proceeds asymmetrically, producing only the correct enantiomer (i.e., the enantiomer which is biologically or physiologically functional). This is not the case in laboratory synthesis, however, and, despite the interest in and energy expended in developing methods by which asymmetric production of a desired chiral molecule (e.g., of a selected enantiomer) can be carried out, there has been only limited success.

In addition to resolving the desired molecule from a racemate of the two enantiomers, it is possible, for example, to produce selected asymmetric molecules by the chiral pool or template method, in which the selected asymmetric molecule is "built" from pre-existing, naturally-occurring asymmetric molecules. Asymmetric homogeneous hydrogenation and asymmetric epoxidation have also been used to produce chiral molecules. Asymmetric hydrogenation is seen as the first manmade reaction to mimic naturally-occurring asymmetric reactions. Sharpless, K. B., Chemistry in Britain, Jan. 1986, 38–44; Mosher, H. S. and J. D. Morrison, Science, 221:1013–1019 (1983); Maugh, T. H., Science, 221:351–354 (1983); Stinson, S., Chemistry and Engineering News, :24 (6/2/86).

Presently-available methods of asymmetric synthesis are limited in their applicability, however. Efficient catalytic asymmetric synthesis reactions are very rare; they require a directing group and thus are substrate limited. Because such reactions are rare and chirality can be exceptionally important in drugs, pheromones and other biologically functional compositions, a catalytic method of asymmetric dihydroxylation would be very valuable. In addition, many naturally-occurring products are dihydroxylated or can be easily derived from the corresponding derivative.

SUMMARY OF THE INVENTION

Olefins or alkenes with or without proximal heteroatom-containing functional groups, are asymmetrically dihydroxylated, oxyaminated or diaminated using an osmium-catalyzed process which is the subject of the present invention. Chiral ligands which are novel alkaloid derivatives, particularly dihydroquinidine derivatives or dihydroquinine derivatives, useful in the method of the present invention are also the subject of the present invention. In the method of asymmetric modification or addition of the present invention, an olefin, a selected chiral ligand, an organic solvent, water, an oxidant, an osmium source and, optionally, an additive which accelerates hydrolysis of the osmate intermediate are combined, under conditions appropriate for reaction to occur. The method of ligand-accelerated catalysis of the present invention is useful to effect asymmetric dihydroxylation, asymmetric oxyamination and asymmetric diamination of an olefin of interest. A particular advantage of the catalytic asymmetric method is that only small quantities of osmium catalyst are required

DETAILED DESCRIPTION OF THE INVENTION

Asymmetric epoxidation has been the subject of much research in the past eight years. Earlier work demonstrated that the titanium-tartrate epoxidation catalyst is actually a complex mixture of epoxidation catalysts in dynamic equilibrium with each other and that the main species present (i.e., the 2:2 structure) is the best catalyst (i.e., about six times more active than titanium isopropoxide bearing no tartrate). This work also showed that this rate advantage is essential to the method's success because it ensures that the catalysis is channeled through a chiral ligand-bearing species.

The reaction of osmium tetroxide (OsO_4) with olefins is a highly selective and reliable organic transformation. It has long been known that this reaction is accelerated by nucleophilic ligands. Criegee, R. et al., *Annal de Chemie*, 550:99 (1942); Ray, R. and D. S. Matteson, *Tetrahedron Letters*, 21:449-450 (1980); Herranz, E. and K. B. Sharpless, *Journal of Organic Chemistry*, 43:2544-2548 (1978). It has now been shown that a highly effective osmium-catalyzed process can be used to replace previously known methods, such as the stoichiometric asymmetric osmylation method. Hentges, S. G. and K. B. Sharpless, *Journal of the American Chemical Society*, 102:4263 (1980). The method of the present invention results in asymmetric induction and enhancement of reaction rate by binding of a selected ligand. Through the use of the ligand-accelerated catalytic method of the present invention, asymmetric dihydroxylation, asymmetric diamination or asymmetric oxyamination can be effected.

As a result of this method, two hydroxyl groups are stereospecifically introduced into (imbedded in) a hydrocarbon framework, resulting in cis vicinal dihydroxylation. The new catalytic method of the present invention achieves substantially improved rates and turnover numbers (when compared with previously-available methods), as well as useful levels of asymmetric induction. In addition, because of the improved reaction rates and turnover numbers, less osmium catalyst is needed in the method of the present invention than in previously-known methods As a result, the expense and the possible toxicity problem associated with previously known methods are reduced.

The method of the present invention is exemplified below with particular reference to its use in the asymmetric dihydroxylation of E-stilbene ($C_6H_5CH:CHC_6H_5$) and trans-3-hexene ($CH_3CH_2CH:CHCH_2CH_3$) The method can be generally described as presented below and that description and subsequent exemplification not only demonstrate the dramatic and unexpected results of ligand-accelerated catalysis, but also make evident the simplicity and effectiveness of the method.

Figure 1:
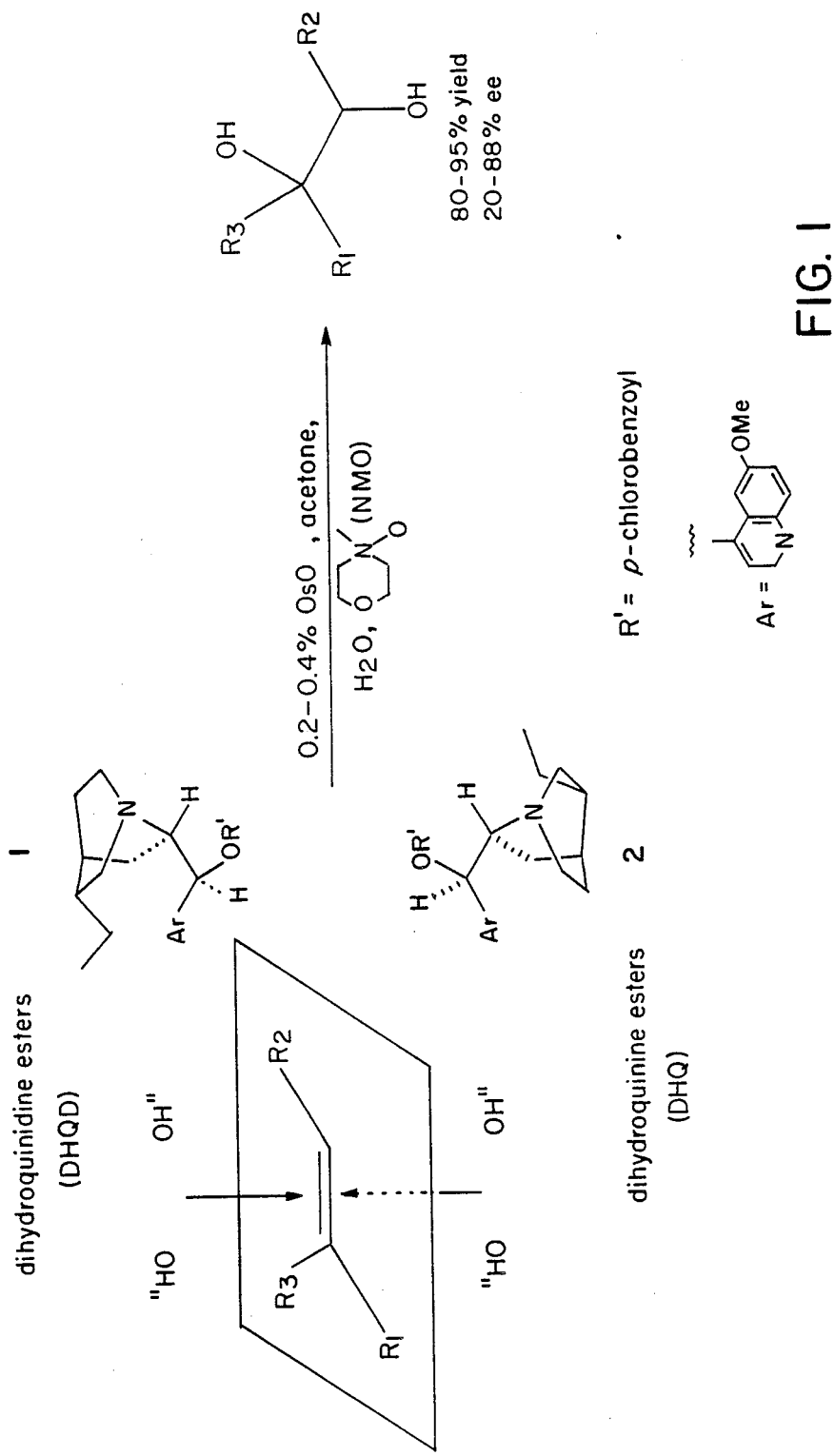
FIG. 1 is a schematic representation of asymmetric dihydroxylation via ligand-accelerated catalysis which is carried out by the method of the present invention.

The asymmetric dihydroxylation method of the present invention is represented by the scheme illustrated in FIG. 1. According to the method of the present invention, asymmetric dihydroxylation of a selected olefin is effected as a result of ligand-accelerated catalysis. That is, according to the method, a selected olefin is combined, under appropriate conditions, with a selected chiral ligand (which in general will be a chiral substituted quinuclidine), an organic solvent, water, an oxidant and osmium tetroxide and, optionally, an acetate compound. In one embodiment, a selected olefin, a chiral ligand, an organic solvent, water and an oxidant are combined; after the olefin and other components are combined, $OsO_4$ is added. The resulting combination is maintained under conditions (e.g., temperature, agitation, etc.) conducive for dihydroxylation of the olefin to occur. Alternatively, the olefin, organic solvent, chiral ligand, water and $OsO_4$ are combined and the oxidant added to the resulting combination. These additions can occur very close in time (i.e., sequentially or simultaneously).

In a preferred embodiment of the present invention, components of the reaction mixture are combined, to form an initial reaction combination, and olefin is added slowly to it, generally with frequent or constant agitation, such as stirring. In this embodiment, organic solvent, chiral ligand, water, $OsO_4$ and the oxidant are combined. The olefin can then be slowly added to the other reactants. It is important that agitation, preferably stirring, be applied during the olefin addition. Surprisingly, for many, if not most olefins, slow addition of the olefin to the initial combination results in better enantiomeric excess (ee), and a faster rate of reaction than the above-described method (i.e., that in which olefin is present at the beginning of the reaction). The beneficial effects (i.e., higher ee's) of slow olefin addition are shown in Table 3 (Column 6). A particular advantage of this slow-addition method is that the scope of the types of olefins to which the asymmetric dihydroxylation method can be applied is greatly broadened. That is, it can be applied to simple hydrocarbon olefins bearing no aromatic substituents, or other function groups. In this process, the olefin is added slowly (e.g., dropwise over time), as necessary to maximize ee. This method is particularly valuable because it results in higher ee and faster reaction times.

In another embodiment of the present method, an additive which accelerates hydrolysis of the osmate intermediate can, optionally, be added to the reaction combination. These additives can be carboxylic acid salts with organic-solubilizing counter-ions (e.g., tetraalkyl ammonium ions). For example, tetraethyl ammonium acetate has been shown to enhance the reaction rate and ee of some olefins (Table 3). The additive can replace the alkaloid in the reaction. Compounds which can be used include benzyltrimethylacetate and tetraethylammonium acetate. However, other oxyanion compounds (e.g., sulfonates or phosphates) may also be useful in hydrolyzing the osmate intermediate. The compound can be added to the reaction combination of organic solvent, chiral ligand, water and $OsO_4$ a reaction vessel, before olefin addition. It is important to agitate (e.g., by stirring) the reaction combination during olefin addition. The additive can also be added to the reaction combination, described above, wherein all of the olefin is added at the beginning of the reaction. In one embodiment, the amount of additive is generally approximately 2 equivalents; in general from about 1 to about 4 equivalents will be used.

The amount of water added to the reaction mixture is an important factor in the instant method. The optimum amount of water to be added can be determined empirically and, in general, should be that amount which results in maximum ee. Generally, approximately 10 to 16 equivalents of water can be added, preferably 13 to 14 equivalents should be used.

An olefin of interest can undergo asymmetric dihydroxylation according to the present invention. For example, any hydrocarbon containing at least one carbon-carbon double bond as a functional group can be asymmetrically dihydroxylated according to the subject method. The method is applicable to any olefin of interest and is particularly well suited to effecting asymmetric dihydroxylation of prochiral olefins (i.e., olefins which can be converted to products exhibiting chirality or handedness). In the case in which the method of the present invention is used to asymmetrically dihydroxylate a chiral olefin, one enantiomer will be more reactive than the other. As a result, it is possible to separate or kinetically resolve the enantiomorphs. That is, through use of appropriately-selected reactants, it is possible to separate the asymmetrically dihydroxylated product from the unreacted starting material and both the product and the recovered starting material will be enantiomerically enriched.

The chiral ligand used in the asymmetric dihydroxylation method will generally be an alkaloid, or a basic nitrogenous organic compound, which is generally heterocyclic and found widely occurring in nature. Examples of alkaloids which can be used as the chiral ligand in the asymmetric dihydroxylation method include cinchona alkaloids, such as quinine, quinidine, cinchonine, and cinchonidine. Examples of alkaloid derivatives useful in the method of the present invention are shown in Table 1. As described in detail below, the two cinchona alkaloids quinine and quinidine act more like enantiomers than like diastereomers in the scheme represented in FIG. 1.

As represented in FIG. 1, and as shown by the results in Table 2, dihydroquinidine derivatives (represented as DHQD) and dihydroquinine derivatives (represented as DHQ) have a pseudo-enantiomeric relationship in the present method (DHQD and DHQ are actually diastereomers). That is, they exhibit opposite enantiofacial selection. Such derivatives will generally be esters, although other forms can be used. When dihydroquinidine is used as the ligand, delivery of the two hydroxyl groups takes place from the top or upper face (as represented in FIG. 1) of the olefin which is being dihydroxylated. That is, in this case direct attack of the re- or re,re- face occurs. In contrast, when the dihydroquinine derivative is the ligand used, the two hydroxyl groups are delivered from the bottom or lower (si- or si,si-face) face of the olefin, again as represented in FIG. 1. This is best illustrated by reference to entries 1, 2 and 5 of Table 2. As shown, when DHQD (dihydroquinidine esters) is used, the resulting diol has an R or R,R configuration and when ligand 2 (dihydroquinine esters) is used, the resulting diol has an S or S,S configuration.

TABLE 1

| | Alkaloid Derivatives | | |
|---|---|---|---|
| R | Derivative | Yield % | % ee |
| 3-ClPH | 3-chlorobenzoyl dihydroquinidine | 89 | 96.5 |
| 2-MeOPh | 2-methoxybenzoyl dihydroquinidine | 89 | 96 |
| 3-MeOPh | 3-methoxybenzoyl dihydroquinidine | 87 | 96.7 |
| 2-NPht | 2-naphtoyl dihydroquinidine cyclohexanoyl dihydroquinidine p-phenylbenzoyl dihydroquinidine | 95.4 | 98.6 |
| Me | Acetyl dihydroquinidine | 72 | 94 |
| Me$_2$N | dimethylcarbamoyl dihydroquinidine | 96 | 95 |
| Ph | benzoyl dihydroquinidine | 92 | 98 |
| 4-MeOPh | 4-methoxybenzoyl dihydroquinidine | 91 | 97.6 |
| 4-ClPh | 4-chlorobenzoyl dihydroquinidine | 93 | 99 |
| 2-ClPh | 2-chlorobenzoyl dihydroquinidine | 87 | 94.4 |
| 4-NO$_2$Ph | 4-nitro benzoyl dihydroquinidine | 71 | 93 |

TABLE 2

| olefin | ligand;ee; contgn.of diai | time |
|---|---|---|
| (styrene) | DHQD; 52%; A DHQ; 53.6%; S | 3 h |
| (β-methylstyrene) | DHQD; 65%; AA DHQ; 55.4%; SS | 5 h |
| (α-methylstyrene) | DHQD; 33%; A | 1.5 h |
| (cinnamyl acetate) | DHQD; 76%; AA | 7 h |
| (stilbene) | DHQD; 98%; AA DHQ; 78.5%; SS | 7 h |

TABLE 2-continued

| olefin | ligand;ee | time |
|---|---|---|
| 2,6-diiodostyrene | DHQD; 65%; | 3 h |
| 4-nitrostyrene | DHQD; 51% | 5 h |
| 4-methoxystyrene | DHQD; 67% | 1 h |
| allylbenzene | DHQD; 20% | 1.5 h |
| (E)-2-hexene | DHQD; 20%; AA | 17 h |
| vinylcyclohexane | DHQD; 46%; A | 1 h |
| styrene-COOCH₂Ph | DHQD; 68% | |
| styrene-OCOPh | DHQD; 80% | |
| styrene | DHQD; 34% | |
| cyclohexyl-COOEt | DHQD; 74.3% | |
| allyl phenyl ether | DHQD; 34% | |
| vinylcyclooctane | DHQD; 50% | |
| nC₁₅H₃₁-CH=CH-COOCH₃ | DHQD; 38% | |
| styrene | DHQD; 0-10% | |

TABLE 2-continued

| olefin | ligand;ee | |
|---|---|---|
| cyclohexene | DHQD; 4.4% | |
| 1-phenylcyclohexene | DHQD; (ca. 10%) | |
| 2-methylstyrene | DHQD; (53%) | |
| 2,5-dimethylstyrene | DHQD; (63%) | |
| 3,4-dimethoxystyrene | DHQD; (ca 5%) | |
| benzyl crotonate | DHQD; (45%) | |
| ethyl crotonate | DHQD; (53%) | |
| 2,5-dimethyl-3-hexene | DHQD; (ca. 12%) | |
| 2-methylallyl phenyl ether | DHQD; (27%) | |

| olefin | ligand;ee contgn. of diai | time |
|---|---|---|
| cinnamaldehyde dimethyl acetal | DHQD; 70% | |
| benzalacetone | DHQD | |
| cinnamyl chloride | DHQD | |
| 4-methyl-2-pentene | DHQD; 37.5% | |

TABLE 2-continued

| | |
|---|---|
| 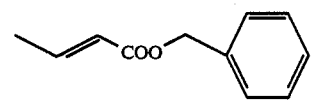 | DHQD; 45% |
| 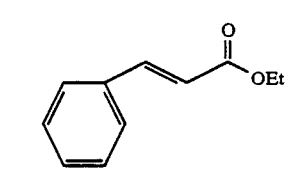 | DHQD |

Because of this face selection rule or phenomenon, it is possible, through use of the present method and the appropriate chiral ligand, to pre-determine the absolute configuration of the dihydroxylation product.

As is also evident in Table 2, asymmetric dihydroxylation of a wide variety of olefins has been successfully carried out by means of the present invention. In each of the cases represented in the Table, the face selection "rule" (as interpreted with reference to the orientation represented in FIG. 1) applied: use of DHQD resulted in attack or dihydroxylation occurring from the top or upper face and use of DHQ resulted in attack or dihydroxylation occurring from the bottom or lower face of the olefin. This resulted, respectively, in formation of

TABLE 3

Enantiomeric excess obtained from asymmetric dihydroxylation of olefins under different conditions

| Entry | Olefins | Stoichiometric[a] | Catalytic[b] (original) | Catalytic[c] (acetate) | Catalytic[d] (slow addition) |
|---|---|---|---|---|---|
| 1 | 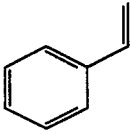 | 61 | 56 | 61 | 60 (5 h) |
| 2 | 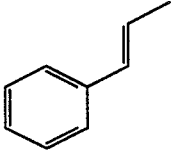 | 90 | 65 | 73 | 91 (5 h) |
| 3 | 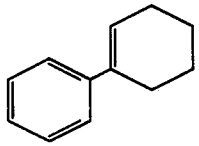 | 81 | 8[e] | 52 | 78 (26 h)[f] |
| 4 | 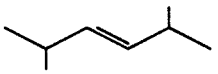 | 82 | 12[g] | 61 | 46 (24 H)[h] 76 (24 h + acetate) |
| 5 | 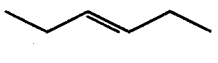 | 72 | 20 | 64 | 70 (16 h) |
| 6 | 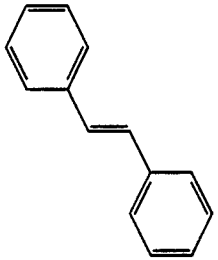 | 89 | 80 | 91.6 | 85 |

[a]All stoichiometric reactions were carried out in acetone-water, 10:1 v/v, at 0° C. and at a concentration of 0.15 M in each reagent.
[b]All reactions were carried out at 0° C. according to the original procedure reported in ref. 1.
[c]All reactions were carried out exactly as described in ref. 1 (i.e. without slow addition) except that 2 eq of Et$_4$NOAc.4H$_2$O were present.
[d]All reactions were carried out at 0° C. as described in note 2 for trans-3-hexene with an alkaloid concentration of 0.25 M. The period for slow addition of the olefin is indicated in parentheses.
[e]With the exception of this case which was 20% complete after 3 days when it was stopped for ee analysis, all other entries in the Table proceeded to completion and gave 85–95% isolated yields of the diols.
[f]With an addition period of 16 h, ee's of 63 and 65% were obtained at 0° C. and 20° C., respectively; with the combination of slow addition over a period of 16 h and the presence of 2 eq of Et$_4$NOAc.4H$_2$O at 0° C., an ee of 81% was realized.
[g]This reaction took 5 days to complete.
[h]When the reaction was carried out at 20° C. and the olefin was added over a period of 24 h, an ee of 59% was obtained.

products having an R or R,R configuration and products having an S or S,S configuration.

In general, the concentration of the chiral ligand used will range from 0.01 M to 2.0 M. In one embodiment, exemplified below, the solution is 0.261M in alkaloid 1 (the dihydroquinidine derivative). In one embodiment of the method, carried out at room temperature, the concentrations of both alkaloids represented in FIG. 1 are at 0.25M. In this way, the enantiomeric excess resulting under the conditions used is maximized. The amount of chiral ligand necessary for the method of the present invention can be varied as the temperature at which the reaction occurs varies. For example, it is possible to reduce the amount of alkaloid (or other chiral ligand) used as the temperature at which the reaction is carried out is changed. For example, if it is carried out, using the dihydroquinidine derivative, at 0° C., the alkaloid concentration can be 0.15M. In another embodiment, carried out at 0° C., the alkaloid concentration was 0.0625M.

Many oxidants (i.e., essentially any source of oxygen) can be used in the present method. For example, amine oxides (e.g., trimethyl amine oxides), tert-butyl hydroperoxide, hydrogen peroxide, and oxygen plus metal catalysts (e.g., copper ($Cu^+$-$Cu^{++}$/$O_2$), platinum ($Pt/O_2$), palladium ($Pd/O_2$) can be used. In one embodiment of the invention, N-methylmorpholine N-oxide (NMO) is used as the oxidant. NMO is available commercially (e.g., Aldrich Chemicals, 97% NMO anhydrous).

Osmium will generally be provided in the method of the present invention in the form of osmium tetroxide ($OsO_4$), although other sources (e.g., osmium trichloride anhydrous, osmium trichloride hydrate) can be used. $OsO_4$ can be added as a solid or in solution.

The osmium catalyst used in the method of the present invention can be recycled, for re-use in subsequent reactions. This makes it possible not only to reduce the expense of the procedure, but also to recover the toxic osmium catalyst. For example, the osmium catalyst can be recycled as follows: Using reduction catalysts (e.g., Pd-C), the osmium VIII species is reduced and adsorbed onto the reduction catalyst. The resulting solid is filtered and resuspended. NMO (or an oxidant), the alkaloid and the substrate (olefin) are added, with the result that the osmium which is bound to the Pd/C solid is reoxidized to $OsO_4$ and re-enters solution and plays its usual catalytic role in formation of the desired diol. This procedure (represented below) can be carried out through numerous cycles, thus re-using the osmium species. The palladium or carbon can be immobilized, for example, in a fixed bed or in a cartridge.

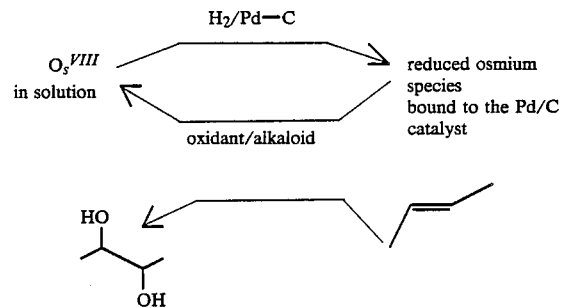

In one embodiment an olefin, such as recrystallised trans-stilbene ($C_6H_5CH{:}CHC_6H_5$), is combined with a chiral ligand (e.g., p-chlorobenzoyl hydroquinidine), acetone, water and NMO. The components can be added sequentially or simultaneously and the order in which they are combined can vary. In this embodiment, after the components are combined, the resulting combination is cooled (e.g., to approximately 0° C. in the case of trans-stilbene); cooling can be carried out using an ice-water bath. $OsO_4$ is then added (e.g., by injection), in the form of a solution of $OsO_4$ in an organic solvent (e.g., in toluene). After addition of $OsO_4$, the resulting combination is maintained under conditions appropriate for the dihydroxylation reaction to proceed.

In another preferred embodiment, a chiral ligand (e.g., dihydroquinidine 4-chlorobenzoate), NMO, acetone, water and $OsO_4$ (as a 5M toluene solution) are combined. The components can be added sequentially or simultaneously and the order in which they are combined can vary. In this embodiment, after the components are combined, the resulting combination is cooled (e.g., to approximately 0° C.557 ); cooling can be carried out using an ice-water bath. It is particularly preferred that the combination is agitated (e.g., stirred). To this well-stirred mixture, an olefin (e.g., trans-3-hexene) is added slowly (e.g., by injection). The rate of addition will depend upon the results obtained, and can be calculated to maximize ee. In the case of trans-3hexene, the olefin was added over a period of about 16–20 hours. After olefin addition, the mixture can be stirred for an addition period of time at the low temperature (1 hour in the case of trans-3-hexene). The slow-addition method is preferred as it results in better ee and faster reaction times.

In another embodiment, a compound which accelerates hydrolysis of the osmate intermediate (e.g., tetraethylammonium acetate) is added to the reaction mixture. The compound (approximately 1-4 equiv.) can be added to the mixture of chiral ligand, water, solvent, oxidant and osmium catalyst and olefin, or prior to the addition of olefin, if the olefin slow-addition method is used.

Figure 4:
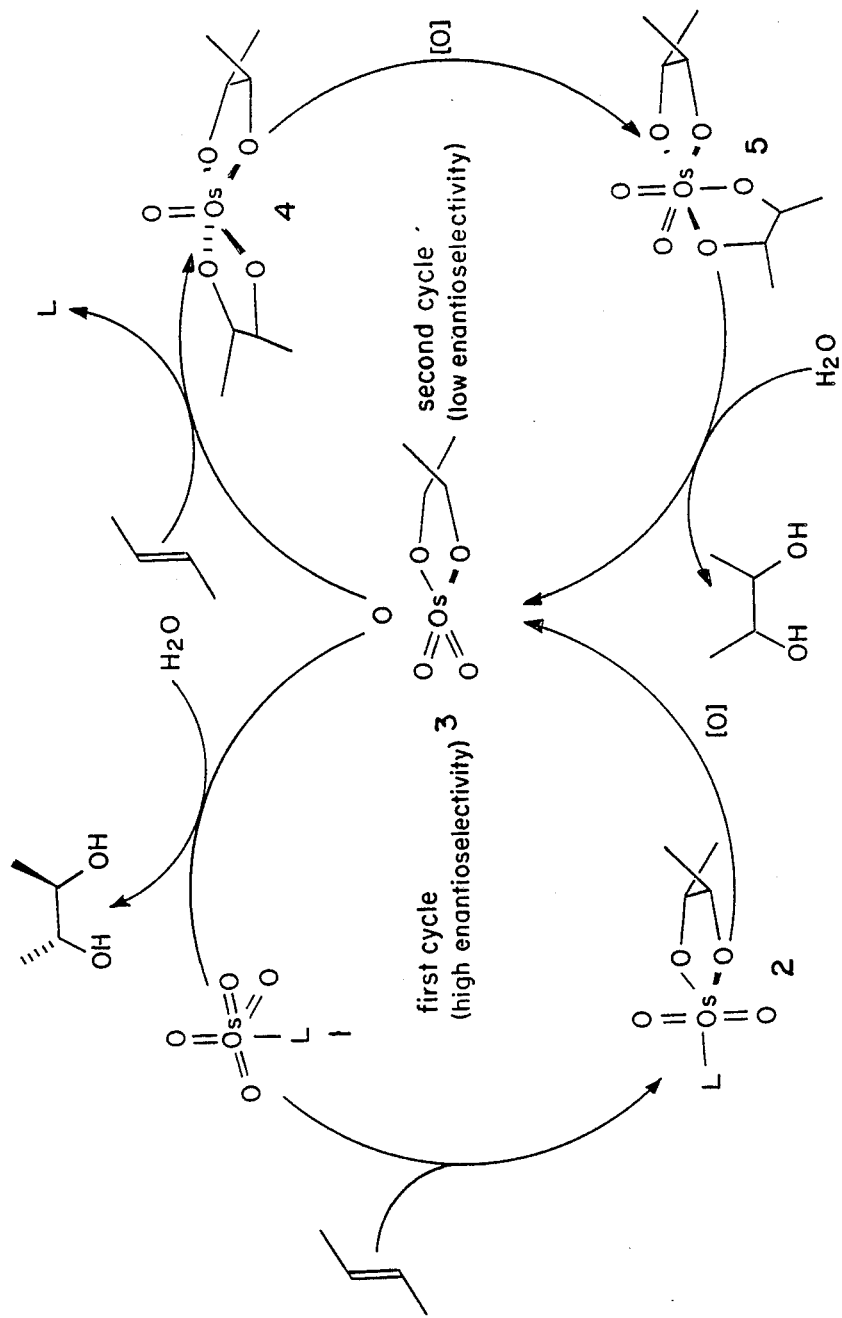
FIG. 4 is a schematic representation of a proposed mechanism of catalytic olefin dihydroxylation. This scheme shows two diol-producing cycles believed to be involved in the ligand-accelerated catalysis of the present invention. Formula 1 represents an alkaloid-osmium complex; formula 2 represents a monoglycolate ester; formula 3 represents an osmium(VIII)trioxoglycolate complex; formula 4 represents a bisglycolate osmium ester; and formula 5 represents a dioxobisglycolate.

The diol-producing mechanistic scheme which it is proposed operates when the slow-addition of olefin method is used is represented in FIG. 4. According to the proposed mechanism, at least two diol-producing cycles exist. As shown in FIG. 4, only the first cycle appears to result in high ee. The key intermediate is the osmium (VIII) triglycolate complex, shown as formula 3 in FIG. 4. This complex occupies the pivotal position at the junction between the two cycles, and determines how diol production is divided between the cycles.

Evidence in favor of the intermediacy of the osmium (VIII) trioxoglycolate complex (formula 3, FIG. 4) is provided by the finding that the events in FIG. 4 can be replicated by performing the process in a stepwise manner under stoichiometric conditions. These experiments were performed under anhydrous conditions in toluene. In the process shown in FIG. 4, one equivalent of the alkaloid osmium complex (shown as formula 1, FIG. 4) is allowed to react with an olefin to give the emerald green monoglycolate ester (formula 2, FIG. 4). A different olefin is then added, followed by an equivalent of an anhydrous amine N-oxide, and rapid formation of the bisglycolate ester (formula 4, FIG. 4) is observed. Upon reductive hydrolysis of the bisglycolate ester, precisely one equivalent of each diol is liberated. These experiments indicate that the second cycle, presumably via the osmium trioxoglycolate complex, is as efficient as the first in producing diols from olefins. Using the same olefin in both can also be used to run this tandem addition sequence When this was done using 1-phenylcyclohexene as the olefin, the ee for the first step was 81% and the ee for the second step was 7% in the opposite direction (i.e., in favor of the minor enantiomer in the first step) Thus, for this substrate any intrusion of the second cycle is particularly damaging, and under the original catalytic conditions 0 1-phenylcyclohexene only gave 8% ee (entry 3, Table 3).

Reduced ee is just part of the counterproductivity of turning on the second cycle; reduced turnover is the other liability. The bisosmate esters (formula 4, FIG. 4) are usually slow to reoxidize the hydrolyze and therefore tend to tie up the catalyst For example, 1-phenylcyclohexene after 3 days under the original conditions underwent only 20% conversion (the 8% ee cited above). With slow addition of the olefin, the oxidation was complete in one day and gave the diol in 95% yield and 78% ee (entry 3, Table 3).

The most important result of the scheme shown in FIG. 4 is the minimization of the second cycle if the olefin is added slowly. Slow addition of the olefin presumably gives the osmium (VIII) trioxoglycolate intermediate sufficient time to hydrolyze so that the osmium catalyst does not get trapped into the second cycle by reacting with olefin. To reiterate, the second cycle not only ruins the ee but also impedes turnover, since some of the complexes involved are slow to reoxidize and/or hydrolyze The optimum feed rate depends on the olefin; it can be determined empirically, as described herein.

The maximum ee obtainable in the catalytic process can be determined during the addition of the alkaloid osmium complex (formula 1, FIG. 4) to the olefin (i.e., the first column in Table 3). Thus, stoichiometric additions can be used to enable one to determine the ee-ceiling which can be reached or approached in the catalytic process if the hydrolysis of 3 (FIG. 4) can be made to dominate the alternative reaction with a second molecule of olefin to give 4 (FIG. 4). In the case of terminal olefins, styrene (Table 3), the trioxoglycolate esters hydrolyze rapidly, since slow addition, or the effect of the osmate-hydrolytic additive give only a slight increase in the ee. However, most olefins benefit greatly from any modification which speeds hydrolysis of the osmate intermediate (3, FIG. 4) (entries 2-5, Table 3), and in extreme cases neither the effect of the osmate-hydrolytic additive nor slow addition is sufficient alone. Diisopropyl ethylene (entry 4, Table 3) approaches its ceiling-ee only when both effects are used in tandem, with slow addition carried out in the presence of acetate. The other entries in the Table reach their optimum ee's through slow addition alone, but even in these cases the addition times can be substantially shortened if a compound, such as a tetraalkyl ammonium acetate, is present.

In many cases, temperature also effects the ee. When the ee is reduced by the second cycle, raising the temperature can often increase it. For example, diisopropyl ethylene gave 46% ee at 0° C. and 59% ee at 25° C. (24h slow addition time in both cases). The rate of hydrolysis of the osmium trioxoglycolate intermediate is apparently more temperature dependent than the rate of its reaction with olefin. This temperature effect is easily rationalized by the expected need to dissociate the chiral ligand from the osmium complex (3) in order to ligate water and initiate hydrolysis, but the ligand need not dissociate for addition of olefin to occur (in fact this second cycle olefin addition step is also likely to be ligand-accelerated).

The following is a description of how optimum conditions for a particular olefin can be determined. To optimize the osmium-catalyzed asymmetric dihydroxylation: (1) If from the known examples there is doubt about what the ceiling-ee is likely to be, it can be determined by performing the osmylation in acetone/water at 0.C; 2) Slow addition at 0° C.: the last column in Table 1 can be used as a guide for choosing the addition time, bearing in mind that at a given temperature each olefin has its own "fastest" addition rate, beyond which the ee suffers as the second cycle turns on. When the olefin addition rate is slow enough, the reaction mixture remains yellow-orange (color of 1, FIG. 4); when the rate is too fast, the solution takes on a blackish tint, indicating that the dark-brown-to-black bisglycolate complex (4, FIG. 4) is being generated; (3) If the ceiling ee is not reached after steps 1 and 2, slow addition plus tetraalkyl ammonium acetate (or other compound which assists hydrolysis of the osmate intermediate) at 0° C. can be used; 4) slow addition plus tetraalkyl ammonium acetate at room temperature can also be used. For all these variations, it is preferable that the mixtures is agitated (e.g., stirred) for the entire reaction period.

The method of the present invention can be carried out over a wide temperature range and the limits of that range will be determined, for example, by the limit of the organic solvent used. The method can be carried out, for example, in a temperature range from room temperature to −10° C. Concentrations of individual reactants (e.g., chiral ligand, oxidant, etc.) can be varied as the temperature at which the method of the present invention is carried out. The saturation point (e.g., the concentration of chiral ligand at which results are maximized) is temperature-related. As explained previously, for example, it is possible to reduce the amount of alkaloid used when the method is carried out at lower temperatures.

The organic solvent used in the present method can be, for example, acetone, acetonitrile, THF, DME, ethanol, methanol, pinacolone, tert butanol or a mixture of two or more organic solvents.

Using the methods described in the Exemplification, HPLC analysis demonstrated that the enantiomeric excess of the resulting diol was 78%.

Figure 2:
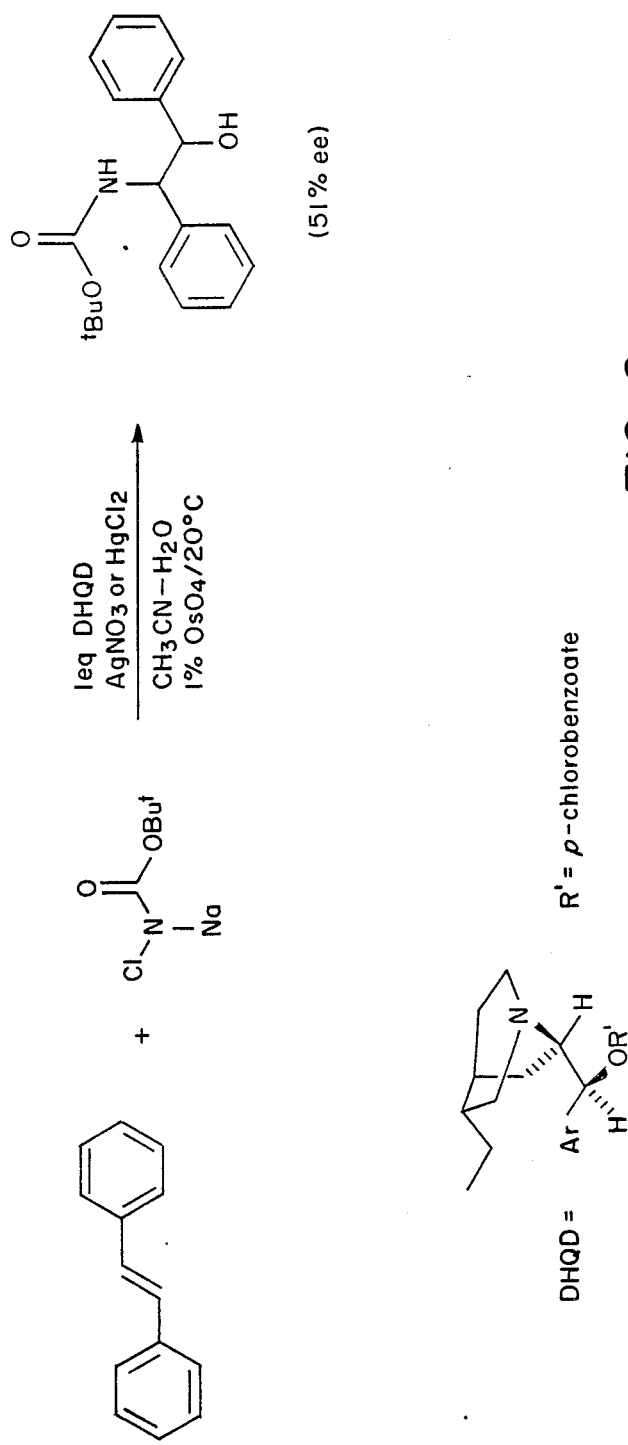
FIG. 2 is a schematic representation of asymmetric catalytic oxyamination of stilbene which is carried out by the method of the present invention.
Figure 3:
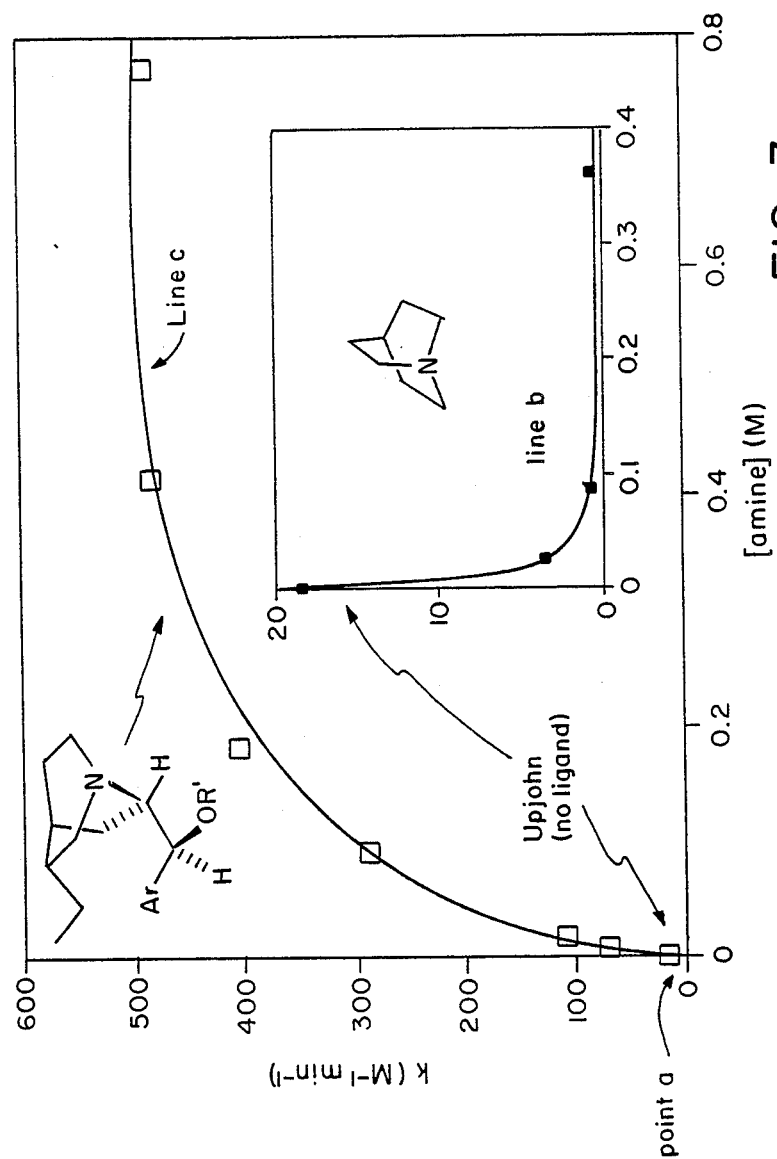
FIG. 3 is a plot of amine concentration vs second-order-rate constant k for the catalytic cis-dihydroxylation of styrene. At point a, no amine has been added. Point a thus represents the rate of the catalytic process in the absence of added amine ligands. Line b represents the rate of the catalytic process in the presence of varying amounts of quinuclidine, a ligand which substantially retards catalysis. Line c represents the rate of the catalytic process in the presence of the dihydroquinidine benzoate derivative 1 represented in FIG. 1. K is defined as $K_{obs}[OsO_4]_o$ where rate = $-d$[styrene]/dt = $K_{obs}$ [styrene]. Conditions: 25° C., $[OsO_4]_o = 4 \times 10^{-4}$ M, $[NMO]_o = 0.2M$ $[styrene]_o = 0.1M$.

In another embodiment of the present invention, styrene was combined with a chiral ligand (DHQD), acetone, water and NMO and $OsO_4$. The plot of amine concentration vs second-order-rate-constant K for the catalytic cis-dihydroxylation of styrene is represented in FIG. 2. The kinetic data of FIG. 2 clearly shows the dramatic effect of ligand-accelerated catalysis achieved by use of the method of the present invention. Point a in FIG. 2 represents the rate of the catalytic process in the absence of amine ligands ($t_{\frac{1}{2}} = 108$ minutes). Line b shows the rates of the process in the presence of varying amounts of quinuclidine, a ligand which substantially retards catalysis (at greater than 0.1M quinuclidine, $t_{\frac{1}{2}}$ is greater than 30 hours). Because of the observed retarding effect of quinuclidine (ligand-decelerated catalysis) the result represented by line C was unexpected. That is, when the process occurs in the presence of dihydroquinidine benzoate derivative 1 (see FIG. 1), the alkaloid moiety strongly accelerates the catalytic process at all concentrations (with ligand 1=0.4M, $t_{\frac{1}{2}}=4.5$ minutes), despite the presence of the quinuclidine moiety.

The rate of the stoichiometric reaction of styrene with osmium tetroxide and that of the corresponding catalytic process were compared. The comparison indicates that both have identical rate constants [$K_{stoic}=(5.1\pm0.1)\times10^2 M^{-1}$ min$^{-1}$ and $K_{cat}=(4.9\pm0.4)\times10^2 M^{-1}$ min$^{-1}$], and that they undergo the same rate acceleration upon addition of ligand 1. Hydrolysis and reoxidation of the reduced osmium species, steps which accomplish catalyst turnover, are not kinetically significant in the catalytic process with styrene. It may be concluded that the limiting step is the same in both processes and consists of the initial addition reaction forming the osmate ester. A detailed mechanistic study reveals that the observed rate acceleration by added ligand 1 is due to formation of an osmium tetroxide-alkaloid complex which, in the case of styrene, is 23 times more reactive than free osmium tetroxide. The rate reaches a maximal and constant value beyond an (approximate) 0.25 M concentration of ligand 1. The onset of this rate saturation corresponds to a pre-equilibrium between DHQD and osmium tetroxide with a rather weak binding constant ($K_{eq}=18\pm2 M-1$). Increasing the concentratrion of DHQD above 0.25 M does not result in corresponding increases in the enantiomeric excess of the product diol. At this concentration of alkaloid, virtually all of the osmium tetroxide already exists as alkaloid complex and raising the concentration further has little effect.

At least in the case of styrene, the rate acceleration in the presence of the alkaloid is accounted for by facilitation of the initial osmylation step. The strikingly opposite effects of quinuclidine and DHQD on the catalysis can be related to the fact that although quinuclidine also accelerates the addition of osmium tetroxide to olefins, it binds too strongly to the resulting osmium(VI) ester intermediate and inhibits catalyst turnover by retarding the hydrolysis/reoxidation steps of the cycle. In contrast the alkaloid appears to achieve a balancing act which renders it near perfect for its role as an accelerator of the dihydroxylation catalysis. It binds strongly enough to accelerate addition to olefins, but not so tightly that it interferes (as does quinuclidine) with subsequent stages of the catalytic cycle. Chelating tertiary amines [e.g., 2,2'-bipyridine and (−)-(R,R)-N,N,N',N'-tetramethyl-1,2cyclohexanediamine) at 0.2M completely inhibit the catalysis. Pyridine at 0.2 M has the same effect.

As represented in Table 2, the method of the present invention has been applied to a variety of olefins. In each case, the face selection rule described above has been shown to apply (with reference to the orientation of the olefin as represented in FIG. 1). That is, in the case of the asymmetric dihydroxylation reaction in which the dihydroquinidine derivative is the chiral ligand, attack occurs on the re- or re,re- face) and in the case in which the dihydroquinine derivative is the chiral ligand, attack occurs on the si- or si,si- face. Thus, as demonstrated by the data presented in the Table 2, the method of the present invention is effective in bringing about catalytic asymmetric dihydroxylation; in all cases, the yield of the diol was 80-95%.

The method of the present invention is also useful to effect asymmetric vicinal diamination and asymmetric vicinal oxyamination of an olefin. In the case of substitution of two nitrogen or of a nitrogen and oxygen, an amino derivative is used as an amino transfer agent and as an oxidant. For example, the olefin to be modified, an organic solvent, water, a chiral ligand, an amino derivative and an osmium-containing compound are combined and the combination maintained under conditions appropriate for the reaction to occur. The amino derivative can be, for example, an N-chlorocarbamate or chloroamine T. Asymmetric catalytic oxyamination of recrystallized trans stilbene, according to the method of the present invention, is represented in FIG. 2.

EXAMPLE 1

Asymmetric Dihydroxylation of Stilbene

The following were placed sequentially in a 2L bottle (or flask): 180.2g (1.0 M) of recrystallised trans stilbene (Aldrich 96%), 62.4g (0.134 moles; 0.134 eq) of the p-chlorobenzoate of hydroquinidine (1), 450 mL of acetone, 86 mL of water (the solution is 0.261 M in alkaloid 1) and 187.2 g (1.6 mol, 1.6 eq.) of solid N-Methylmorpholine N-Oxide (NMO, Aldrich 97%). The bottle was capped, shaken for 30 seconds, cooled to 0-4° C. using an ice-water bath. OsO$_4$ (4.25 mL of a solution prepared using 0.120 g OsO$_4$/mL toluene; 0.002 Mol%; 0.002 eq.) was injected. The bottle was shaken and placed in a refrigerator at ca. 4° C. with occasional shaking. A dark purple color developed and was slowly replaced by a deep orange one; the heterogeneous reaction mixture gradually became homogeneous and at the end of the reaction, a clear orange solution was obtained The reaction can be conveniently monitored by TLC (silicagel; CH$_2$C$_{12}$; disappearance of the starting material at a defined Rf). After 17 hours, 100g of solid sodium metabisulfite (Na$_2$S$_2$O$_5$) were added, the reaction mixture was shaken (1 minute) and left at 20° C. during 15 minutes. The reaction mixture was then diluted by an equal volume of CH$_2$C$_{12}$ and anhydrous Na$_2$S0$_4$ added (100 g). After another 15 minutes, the solids were removed by filtration through a pad of celite, washed three times with 250 mL portions of CH$_2$C$_{12}$ and the solvent was evaporated under vacuum (rotatory-evaporator, bath temperature=30°-35° C.)

The crude oil was dissolved in ethyl acetate (750 mL), extracted three times with 500 ml. portions of 2.0 M HCl, once with 2.0 M NaOH, dried over Na$_2$S0$_4$ and concentrated in vacuo to leave 190 g (89%) of crude diol 2 as a pale yellow solid. The enantiomeric excess of the crude diol 2 was determined by HPLC analysis of the derived bis-acetate (Pirkle IA column using 5% isopropanol/hexane mixture as eluant. Retention times are: t1=18.9 minutes; t2=19.7 minutes. Recrystallisation from about 1000 ml. CH$_2$C$_{12}$ gave 150 g (70%) of pure diol 2 (ee=90%). ee (enantiomeric excess) is calculated from the relationship (for the R enantiomer, for example): percent e.e.=[(R)-(S)/[(R)+(S)]×100.

The aqueous layer was cooled to 0° C. and treated with 2.0M NaOH (about 500 mL) until pH=7. Methylene chloride was added (500 mL) and the pH adjusted to 10-11 using more 2.OM NaOH (about 500 mL). The aqueous layer was separated, extracted twice with methylene chloride (2×300 mL) and the combined organic layers were dried over Na$_2$SO$_4$ The solvent was removed in vacuo to provide the alkaloid 1 as a yellow foam. The crude alkaloid was dissolved in ether (1000 mL), cooled to 0° C. (ice-bath) and treated with dry HCl until acidic pH (about 1-2). The faint yellow precipitate of p-chlorobenzoylhydroquinidine hydrochloride was collected by filtration and dried under high vacuum (0.01mm Hg).

The free base was liberated by suspending the salt in ethyl acetate (500 mL), cooling to 0° C. and adding 28% $NH_4OH$ until pH=11 was reached. After separation, the aqueous layer was extracted twice with ethyl acetate, the combined organic layers were dried over $Na_2SO_4$ and the solvent removed in vacuo to give the free base as a white foam.

EXAMPLE 2

Asymmetric Dihydroxylation of Stilbene

Asymmetric dihydroxylation of stilbene was carried out as described in Example 1, except that 1.2 equivalents of NMO were used.

EXAMPLE 3

Asymmetric Dihydroxylation of Stilbene

Asymmetric dihydroxylation of stilbene was carried out as described in Example 1, except that 1.2 equivalents of NMO, as a 62% wt. solution, were used.

EXAMPLE 4

Preparation of dihydroquinidine derivative

Preparation of dihydroquinidine by catalytic reduction of quinidine

To a solution of 16.2 g of quinidine (0.05 mol) in 150mL of 10% $H_2SO_4$ (15 g conc $H_2SO_4$ in 150mL $H_2O$) was added 0.2 g of $PdCl_2$ (0.022 eq; 0.0011 mol). The reaction mixture was hydrogenated in a Parr shaker at 50 psi pressure. After 2h, the catalyst was removed by filtration through a pad of celite and washed with 150mL of water. The faint yellow solution so obtained was slowly added to a stirred aqueous NaOH solution (15 g of NaOH in 150mL $H_{20}$. A White precipitate immediately formed and the pH of the solution was brought to 10-11 by addition of excess aqueous 15% NaOH. The precipitate was collected by filtration, pressed dry and suspended in ethanol (175mL). The boiling solution was quickly filtered and upon cooling to room temperature, white needles crystallized out. The crystals were collected and dried under vacuum (90° C.; 0.05 mm Hg) overnight. This gave 8.6 g (52.7%) of pure dihydroquinidine mp=169.5°-170° C. The mother liquor was placed in a freezer at 15° C. overnight. After filtration and drying of the crystals, another 4.2 g (21.4%) of pure material was obtained, raising the total amount of dihydroquinidine to 12.8 g (74.1%).

Preparation of dihydroquinidine p-chlorobenzoate (ligand 1)

From dihydroquinidine hydrochloride (Aldrich)

To a cooled (0° C.) suspension of 100 g dihydroquinidine hydrochloride (0.275 mol) in 300mL of dry $CH_2C_{12}$ was added, over 30 minutes with efficient stirring, 115mL of $Et_3N$ (0.826 eq; 3 eqs) dissolved in 50mL of $CH_2C_{12}$ The dropping funnel was rinsed with an additional 20mL of $CH_2C_{12}$ After stirring 30 minutes at 0° C., 42mL of p-chlorobenzoyl chloride (0.33 mol;57.8g; 1 2 eq) dissolved in 120mL of $CH_2C_{12}$ was added dropwise over a period of 2h. The heterogeneous reaction mixture was then stirred 30 minutes at O° C. and 1 hour at room temperature; 700mL of a 3.OM NaOH solution was then slowly added until pH=10-11 was obtained. After partitioning, the aqueous layer was extracted with three 100ml of $CH_2Cl_2$. The combined organic layers were dried over $Na_2SO_4$ and the solvent removed in vacuo (rotatory evaporator). The crude oil was dissolved in 1L of ether, cooled to 0° C. and treated with HCl gas until the ether solution gives a pH of about 2 using wet pH paper. The slightly yellow precipitate was collected and dried under vacuum to give 126 g (91.5%) of dihydroquinidine p-chlorobenzoate hydrochloride.

The salt was suspended in 500mL of ethyl acetate, cooled to 0° C. and treated with 28% $NH_4OH$ until pH=11 was reached. After separation, the aqueous layer was extracted with two 200mL portions of ethyl acetate. The combined organic layers were dried over $Na_2SO_4$ and the solvent removed under vacuum, leaving the free base 1 as a white foam (112g; 88% overall). $[a]^{25}D -59.1°$ (c 1.0, EtOH); IR (CH 2940, 2860, 1720, 1620, 1595, 1520, 1115, 1105, 1095, 1020 cm.$^{-1}$; $^1H$ NMR (CDCl$_3$) 8.72 (d, 1H, J=5 Hz), 8.05 (br d, 3H, J=9.7 Hz), 7.4 (m, 5H), 6.72 (d, 1H, J=7.2 Hz), 3.97 (s, 3H), 3.42 (dd, 1H, J=9, 19.5 Hz), 2.9-2.7 (m, 4H), 1.87 (m, 1H), 1.75 (br s, 1H), 1.6-1.45 (m, 6H), 0.92 (t, 3H, J=7 Hz). Anal. Calcd for $C_{27}H_{29}ClN_2O_3$: C, 69.74; H, 6.28; Cl, 7.62; N, 6.02. Found: C, 69.95;H, 6.23; Cl, 7.81; N, 5.95.

From dihydroquinidine

To a 0° C. solution of 1.22g dihydroquinidine (0.0037 mol) in 30mL of $CH_2Cl_2$ was added 0.78mL of $Et_3N$ (0.0056 mol; 1.5 eq), followed by 0.71mL of p-chlorobenzoyl chloride (0.005 mol; 2 eq) in 1mL $CH_2Cl_2$ After stirring 30 minutes at 0° C. and 1 hour at room temperature, the reaction was quenched by the addition of 10% $Na_2CO_3$ (20mL). After separation, the aqueous layer was extracted with three 10mL portions of $CH_2Cl_2$. The combined organic layers were dried over $Na_2SO_4$ and the solvent removed under vacuum. The crude product was purified as described above. Dihydroquinidine p-chlorobenzoate (1) was obtained in 91% yield (1.5g) as a white foam.

Recovery of dihydroquinidine p-chlorobenzoate

The aqueous acidic extracts (see EXAMPLE 1) were combined, cooled to 0° C. and treated with 2.OM NaOH solution (500mL) until pH=7 was obtained. Methylene chloride was added (500mL) and the pH was adjusted to 10-11 using more 2.0M NaOH. The aqueous layer was separated and extracted with two 300mL portions of $CH_2Cl_2$. The combined organic layers were dried over $Na_2SO_4$ and concentrated to leave the crude alkaloid as a yellow foam. The crude dihydroquinidine p-chlorobenzoate (1) was dissolved in 1L of ether, cooled to 0° C. and HCl gas was bubbled into the solution until a pH of 1-2 was obtained using wet pH paper. The pale yellow precipitate of 1 as the hydrochloride salt was collected by filtration and dried under high vacuum (0.01mm Hg). The free base was liberated by suspending the salt in 500mL of ethyl acetate, cooling the heterogeneous mixture to 0° C. and adding 28% $NH_4OH$ (or 15% NaOH) until pH=11 was obtained. After separation, the aqueous layer was extracted with two 100mL portions of ethyl acetate, the combined organic layers were dried over $Na_2SO_4$ and the solvent removed in vacuo to give 56g (91% recovery) of pure dihydroquinidine p-chlorobenzoate (1) as a white foam.

EXAMPLE 5

Preparation of dihydroquinine derivative

Preparation of dihydroquinine p-chlorobenzoate

The catalytic hydrogenation and p-chlorobenzoylation were conducted as described for the dihydroquinidine p-chlorobenzoate. The physical properties of dihydroquinine p-chlorobenzoate 2 are as follows: $[\alpha]^{25}D + 142.1$ (c 1.0, EtOH); IR (CH$_2$Cl$_2$) 2940, 2860, 1720, 1620, 1595, 1508, 1115, 1105, 1095, 1020 cm$^{-1}$, $^1$H NMR (CDCl$_3$) d 8.72 (d, 1H, J=5 Hz), 8.05 (br d, 3H, J=8 Hz), 7.4 (m, 5H), 6.7 (d, 1H, J=8 Hz), 4.0 (s, 3H), 3.48 (dd, 1H, J=8.5, 15.8 Hz), 3.19 (m, 1H), 3.08 (dd, 1H, J=11, 15 Hz), 2.69 (ddd, 1H, J=5, 12, 15.8 Hz), 2.4 (dt, 1H, J=2.4, 15.8 Hz), 1.85–1.3 (m, 8H), 0.87 (t, 3H, J=Hz). Anal. Calcd for C$_{27}$H$_{29}$ClN$_2$O$_3$: C, 69.74; H, 6.28; Cl, 7.62; N, 6.02. Found: C, 69.85; H, 6.42; Cl, 7.82; N, 5.98.

Recovery of dihydroquinine p-chlorobenzoate (2)

The procedure is identical to that described above for recovery of 1.

EXAMPLE 6

Procedure for Asymmetric Dihydroxylation of Trans-3-hexene Under "Slow Addition" Conditions To a well stirred mixture of 0.465g (1 mmol, 0.25 eq=0.25M in L) dihydroquinidine 4-chlorobenzoate (Aldrich, 98%), 0.7g (6 mmol, 1.5 eq) N-methylmorpholine N-oxide (Aldrich, 97%), and 32 L of a 0.5M toluene solution of osmium tetroxide (16 mol, 4×10$^{-3}$ equiv), in 4 mL of an acetone-water mixture (10:1 v/v) at 0° C., neat 0.5 mL (0.34g, 4 mmol) trans-3-hexene (Wiley, 99.9%) was added slowly, via a gas tight syringe controlled by a syringe pump and with the tip of the syringe needle immersed in the reaction mixture, over a period of 16 h. The mixture gradually changed from heterogeneous to homogeneous. After the addition was complete, the resulting clear orange solution was stirred at 0° C. for an additional hour. Solid sodium metabisulfite (Na$_2$S$_2$O$_5$, 1.2g) was added and the mixture was stirred for 5 min, and then diluted with dichloromethane (8mL) and dried (Na$_2$SO$_4$). The solids were removed by filtration, and washed three times with dichloromethane. The combined filtrates were concentrated, and the residual oil was subjected to flash column chromatography on silica gel (25g, elution with diethyl ether-dichloromethane, 2:3 v/v, R$_f$ 0.33) and collection of the appropriate fractions afforded 0.30–0.32g (85–92% yield) of the hexanediol. The enantiomeric excess of the diol was determined by GLC analysis (5% phenyl-methylsilicone, 0.25 m film, 0317 mm diameter, 29 m long) of the derived bis-Mosher ester to be 70%.

EXAMPLE 7

Asymmetric Dihydroxylation of 1-Phenylcyclohexene with Et$_4$NOAc-4H$_2$O

The procedure set out in EXAMPLE 1 was followed, except that 1-phenylcyclohexene (1.OM) was substituted for trans-stilbene. The reaction was allowed to proceed for three days, after which only 20% conversion to the diol was obtained (8% ee).

The above procedure was repeated, with the difference that 2 equivalents of tetraethyl ammonium acetate (Et$_4$NOAc-4H$_2$O) was added to the reaction mixture at the beginning of the reaction. Fifty-two (52%) percent ee was obtained using this procedure.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. A method of ligand-accelerated, osmium-catalyzed asymmetric dihydroxylation of an olefin, comprising combining the olefin, a selected chiral ligand, wherein the chiral ligand comprises a dihydroquinine derivative or a dihydroquinidine derivative, acetone, water, an amine oxide and an osmium-containing compound in sufficient quantity to provide a catalytic amount of osmium, under conditions appropriate for asymmetric dihydroxylation of the olefin to occur.

2. A method of claim 5 wherein the amine oxide is N-methylmorpholine N-oxide and the osmium-containing compound is osmium tetroxide.

3. A method of claim 1 further comprising adding tetraethylammonium acetate.

4. An osmium-catalyzed, ligand-accelerated method of asymmetric dihydroxylation of an olefin, comprising the steps of:
   a. combining the olefin, a dihydroquinone derivative or a dihydroquinidine derivative, an organic solvent, water and a selected amine oxide;
   b. adding an osmium-containing catalyst to the combination formed in (a), in sufficient quantity to provide a catalytic amount of osmium to the combination in (a); and
   c. maintaining the resulting combination produced in (b) under conditions appropriate for asymmetric dihydroxylation of the olefin to occur.

5. An osmium-catalyzed, ligand-accelerated method for producing an asymmetrically dihydroxylated olefin, comprising:
   a. combining (1) a dihydroquinine derivative or a dihydroquinidine derivative, (2) an organic solvent, (3) N-methylmorpholine N-oxide, (4) a tetraalkyl ammonium compound, and (5) an osmium tetroxide catalyst; and
   b. adding the olefin slowly to the combination formed in (a) under conditions appropriate for dihydroxylation of the olefin to occur.

6. A method of claim 5 wherein the tetraalkyl ammonium compound is tetraethylammonium acetate.

7. A method of ligand-accelerated, osmium-catalyzed, asymmetric dihydroxylation of an olefin, comprising the steps of:
   a. combining the olefin, a cinchona alkaloid derivative, an organic solvent, water and a selected amine oxide;
   b. adding an osmium-containing compound in sufficient quantity to provide a catalytic amount of osmium to the combination formed in (a);
   c. maintaining the resulting combination produced in (b) under conditions appropriate for asymmetric dihydroxylation of the olefin to occur.

8. A method of claim 7 wherein the cinchona alkaloid derivative is a dihydroquinidine derivative or a dihydroquinine derivative, the amine oxide is N-methylmorpholine N-oxide and the osmium-containing compound is osmium tetroxide.

9. A method of ligand-accelerated, osmium-catalyzed, asymmetric dihydroxylation of an olefin, comprising the steps of:

a. combining a cinchona alkaloid derivative, an organic solvents, water and a selected amine oxide;

b. adding an osmium-containing compound in sufficient quantity to provide a catalytic amount of osmium to the combination formed in (a);

c. adding the olefin slowly to the combination formed in (b) under conditions appropriate for asymmetric dihydroxylation of the olefin to occur.

10. A method of claim 9 wherein the cinchona alkaloid derivative is a dihydroquinidine derivative or a dihydroquinine derivative, the amine oxide is N-methylmorpholine N-oxide, the osmium-containing catalyst is osmium tetroxide and the organic solvent is acetone.

11. A method of claim 10 further comprising adding a tetraalkylammonium compound to the mixture formed in (a).

* * * * *